United States Patent
McLean et al.

(10) Patent No.: US 9,949,844 B2
(45) Date of Patent: Apr. 24, 2018

(54) APPARATUS FOR USE IN SPINAL INTERBODY FUSION

(71) Applicant: SPINE WAVE, INC., Shelton, CT (US)

(72) Inventors: Scott McLean, Sandy Hook, CT (US); Fabio Amaral Pinto, Stamford, CT (US); Peter Barreiro, West Haven, CT (US); David Boisvert, Meriden, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 15/373,587

(22) Filed: Dec. 9, 2016

(65) Prior Publication Data

US 2017/0095347 A1   Apr. 6, 2017

Related U.S. Application Data

(60) Continuation of application No. 14/550,258, filed on Nov. 21, 2014, now Pat. No. 9,517,141, which is a division of application No. 13/795,054, filed on Mar. 12, 2013, now Pat. No. 8,900,312.

(51) Int. Cl.
*A61F 2/44* (2006.01)
*A61F 2/46* (2006.01)
*A61F 2/30* (2006.01)

(52) U.S. Cl.
CPC .............. *A61F 2/447* (2013.01); *A61F 2/442* (2013.01); *A61F 2/4601* (2013.01);
(Continued)

(58) Field of Classification Search
CPC .. A61F 2002/4629; A61F 2/44; A61F 2/4455; A61F 2/446; A61F 2/4465; A61F 2/447

USPC ................................ 623/17.11–17.16; 606/99
See application file for complete search history.

(56) References Cited

U.S. PATENT DOCUMENTS 3,486,505 A   12/1969   Morrison
4,524,766 A   6/1985   Petersen
(Continued)

FOREIGN PATENT DOCUMENTS

EP   0621020 A1   10/1994
FR   2639823 A1   6/1990
(Continued)

OTHER PUBLICATIONS

PCT Search Report for corresponding PCT Application No. PCT/US2008/064534, dated Sep. 12, 2008.
(Continued)

*Primary Examiner* — Matthew Lawson
(74) *Attorney, Agent, or Firm* — Hoffmann & Baron, LLP

(57) ABSTRACT

An expandable interbody fusion device includes superior and inferior endplates that are configured to receive a sequentially inserted stack of expansion members or wafers in interlocking engagement. The expansion members are formed to each have a generally U-shaped rearward facing opening. The superior and inferior endplates have openings through their outer surfaces in at least partial alignment and communication with the rearward facing openings of the expansion members. The inferior endplate has a fully bounded cavity for telescoping receipt of the superior endplate. The inferior endplate also has a fully bounded channel extending through the rear endwall thereof in direct communication with the rearward facing opening of at least one expansion member for the receipt of bone graft material into the device to promote fusion between opposing vertebral bodies of the spine.

15 Claims, 11 Drawing Sheets

(52) U.S. Cl.
CPC ....... *A61F 2/4611* (2013.01); *A61F 2002/305* (2013.01); *A61F 2002/3093* (2013.01); *A61F 2002/30131* (2013.01); *A61F 2002/30383* (2013.01); *A61F 2002/30401* (2013.01); *A61F 2002/30579* (2013.01); *A61F 2002/30599* (2013.01); *A61F 2002/30601* (2013.01); *A61F 2002/30604* (2013.01); *A61F 2002/30611* (2013.01); *A61F 2002/30774* (2013.01); *A61F 2002/30777* (2013.01); *A61F 2002/30784* (2013.01); *A61F 2002/30828* (2013.01); *A61F 2002/4475* (2013.01); *A61F 2002/4623* (2013.01); *A61F 2002/4627* (2013.01)

(56) References Cited

U.S. PATENT DOCUMENTS

| | | | |
|---|---|---|---|
| 4,683,476 A | 7/1987 | Ferrari et al. | |
| 4,736,738 A | 4/1988 | Lipovsek et al. | |
| 4,743,493 A | 5/1988 | Sioshansi et al. | |
| 4,755,797 A | 7/1988 | Kanaya | |
| 4,863,476 A | 9/1989 | Shepperd | |
| 4,888,024 A | 12/1989 | Powlan | |
| 5,059,193 A | 10/1991 | Kuslich | |
| 5,192,326 A | 3/1993 | Bao et al. | |
| 5,192,327 A | 3/1993 | Brantigan | |
| 5,197,971 A | 3/1993 | Bonutti | |
| 5,298,254 A | 3/1994 | Prewett et al. | |
| 5,431,658 A | 7/1995 | Moskovich | |
| 5,439,684 A | 8/1995 | Prewett et al. | |
| 5,505,732 A | 4/1996 | Michelson | |
| 5,514,180 A | 5/1996 | Heggeness et al. | |
| 5,522,899 A | 6/1996 | Michelson | |
| 5,571,109 A | 11/1996 | Bertagnoli | |
| 5,591,235 A | 1/1997 | Kuslich | |
| 5,645,599 A | 7/1997 | Samani | |
| 5,702,454 A | 12/1997 | Baumgartner | |
| 5,755,797 A | 5/1998 | Baumgartner | |
| 5,756,127 A | 5/1998 | Grisoni et al. | |
| 5,766,252 A | 6/1998 | Henry et al. | |
| 5,836,948 A | 11/1998 | Zucherman et al. | |
| 5,860,977 A | 1/1999 | Zucherman et al. | |
| 5,891,147 A | 4/1999 | Moskovitz et al. | |
| 5,951,553 A | 9/1999 | Betz et al. | |
| 5,980,522 A | 11/1999 | Koros et al. | |
| 6,033,411 A | 3/2000 | Preissman | |
| 6,045,579 A | 4/2000 | Hochshuler et al. | |
| 6,066,154 A | 5/2000 | Reiley et al. | |
| 6,074,390 A | 6/2000 | Zucherman et al. | |
| 6,110,179 A | 8/2000 | Flivik et al. | |
| 6,110,210 A | 8/2000 | Norton et al. | |
| 6,159,211 A | 12/2000 | Boriani et al. | |
| 6,159,244 A | 12/2000 | Suddaby | |
| 6,190,414 B1 | 2/2001 | Young et al. | |
| 6,200,347 B1 | 3/2001 | Anderson et al. | |
| 6,241,771 B1 | 6/2001 | Gresser et al. | |
| 6,273,916 B1 | 8/2001 | Murphy | |
| 6,279,916 B1 | 8/2001 | Stecher | |
| 6,287,308 B1 | 9/2001 | Betz et al. | |
| 6,287,309 B1 | 9/2001 | Baccelli et al. | |
| 6,290,724 B1 | 9/2001 | Marino | |
| 6,387,130 B1 | 5/2002 | Stone et al. | |
| 6,395,034 B1 | 5/2002 | Suddaby | |
| 6,402,750 B1 | 6/2002 | Atkinson et al. | |
| 6,419,705 B1 | 7/2002 | Erickson | |
| 6,432,107 B1 | 8/2002 | Ferree | |
| 6,436,142 B1 | 8/2002 | Paes et al. | |
| 6,478,800 B1 | 11/2002 | Fraser et al. | |
| 6,488,710 B2 | 12/2002 | Besselink | |
| 6,500,205 B1 | 12/2002 | Michelson | |
| 6,520,993 B2 | 2/2003 | James et al. | |
| 6,562,074 B2 | 5/2003 | Gerbec et al. | |
| 6,595,998 B2 | 7/2003 | Johnson et al. | |
| 6,620,196 B1 | 9/2003 | Trieu | |
| 6,648,917 B2 | 11/2003 | Gerbec et al. | |
| 6,656,178 B1 | 12/2003 | Veldhuizen et al. | |
| 6,726,691 B2 | 4/2004 | Osorio et al. | |
| 6,740,093 B2 | 5/2004 | Hochschuler et al. | |
| 6,837,904 B2 | 1/2005 | Ralph et al. | |
| 6,852,095 B1 | 2/2005 | Ray | |
| 6,852,126 B2 | 2/2005 | Ahlgren | |
| 6,852,129 B2 | 2/2005 | Gerbec et al. | |
| 6,863,673 B2 | 3/2005 | Gerbec et al. | |
| 6,997,929 B2 | 2/2006 | Manzi et al. | |
| 7,094,257 B2 | 8/2006 | Mujwid et al. | |
| 7,118,580 B1 | 10/2006 | Beyersdorff et al. | |
| 7,591,852 B2 | 9/2009 | Prosser | |
| 7,780,732 B2 | 8/2010 | Abernathie | |
| 7,918,891 B1 | 4/2011 | Curran et al. | |
| 7,931,688 B2 | 4/2011 | Landry et al. | |
| 7,967,867 B2 | 6/2011 | Barreiro et al. | |
| 8,062,375 B2 | 11/2011 | Glerum et al. | |
| 8,303,663 B2 | 11/2012 | Jimenez et al. | |
| 8,303,879 B2 | 11/2012 | Bertele et al. | |
| 8,308,805 B2 | 11/2012 | Lynn et al. | |
| 8,337,562 B2 | 12/2012 | Landry et al. | |
| 8,382,842 B2 | 2/2013 | Greenhalgh et al. | |
| 8,491,658 B1 | 7/2013 | Etminan | |
| 8,628,578 B2 | 1/2014 | Miller et al. | |
| 8,795,369 B1 | 8/2014 | Pimenta et al. | |
| 2002/0026195 A1 | 2/2002 | Layne et al. | |
| 2002/0147497 A1 | 10/2002 | Belef et al. | |
| 2002/0177897 A1 | 11/2002 | Michelson | |
| 2002/0183761 A1 | 12/2002 | Johnson et al. | |
| 2003/0074064 A1* | 4/2003 | Gerbec ............... A61F 2/4455 623/16.11 |
| 2003/0171812 A1 | 9/2003 | Grunberg et al. | |
| 2004/0019354 A1 | 1/2004 | Johnson et al. | |
| 2004/0054412 A1 | 3/2004 | Gerbec et al. | |
| 2004/0064144 A1 | 4/2004 | Johnson et al. | |
| 2004/0162618 A1 | 8/2004 | Mujwid et al. | |
| 2004/0220580 A1 | 11/2004 | Johnson et al. | |
| 2004/0230198 A1 | 11/2004 | Manzi et al. | |
| 2005/0027364 A1 | 2/2005 | Kim et al. | |
| 2005/0033429 A1* | 2/2005 | Kuo ..................... A61F 2/447 623/17.11 |
| 2005/0149194 A1 | 7/2005 | Ahlgren | |
| 2005/0283244 A1 | 12/2005 | Gordon et al. | |
| 2006/0058807 A1 | 3/2006 | Landry et al. | |
| 2006/0058880 A1 | 3/2006 | Wysocki et al. | |
| 2006/0129244 A1 | 6/2006 | Ensign | |
| 2008/0021558 A1* | 1/2008 | Thramann ............... A61F 2/447 623/17.16 |
| 2008/0154377 A1 | 6/2008 | Voellmicke | |
| 2008/0161927 A1 | 7/2008 | Savage et al. | |
| 2008/0172127 A1 | 7/2008 | Perez-Cruet et al. | |
| 2008/0300598 A1 | 12/2008 | Barreiro et al. | |
| 2009/0138086 A1 | 5/2009 | Dewey | |
| 2009/0198339 A1 | 8/2009 | Kleiner et al. | |
| 2010/0179594 A1 | 7/2010 | Theofilos et al. | |
| 2010/0179656 A1 | 7/2010 | Theofilos | |
| 2010/0292796 A1 | 11/2010 | Greenhalgh et al. | |
| 2010/0312347 A1 | 12/2010 | Arramon et al. | |
| 2012/0022653 A1 | 1/2012 | Kirschman | |
| 2012/0123548 A1* | 5/2012 | Lynn ..................... A61F 2/442 623/17.16 |
| 2012/0158144 A1 | 6/2012 | Ullrich, Jr. et al. | |
| 2012/0191190 A1 | 7/2012 | Trieu | |
| 2012/0197405 A1 | 8/2012 | Cuevas et al. | |
| 2012/0226357 A1 | 9/2012 | Varela | |
| 2012/0253406 A1 | 10/2012 | Bae et al. | |
| 2013/0090735 A1 | 4/2013 | Mermuys et al. | |
| 2013/0190875 A1* | 7/2013 | Shulock ............... A61F 2/441 623/17.12 |
| 2014/0148903 A1 | 5/2014 | Pinto | |

FOREIGN PATENT DOCUMENTS

| | | |
|---|---|---|
| FR | 2719763 A1 | 11/1995 |
| JP | 2004525692 A | 8/2004 |
| JP | 2006517836 A | 8/2006 |
| JP | 2011513001 A | 4/2011 |

(56) References Cited

FOREIGN PATENT DOCUMENTS

| | | |
|---|---|---|
| WO | 9902214 A1 | 1/1999 |
| WO | 02/071921 A2 | 9/2002 |
| WO | 2009/114381 A1 | 9/2009 |

OTHER PUBLICATIONS

Baddeley, S. and Cullen, J.C., "The Use of Methylmethacrylate in the Treatment of Giant Cell Tumours of the Proximal Tibia", Aust. N.Z. J. Surg. vol. 49—No. 1, Feb. 1979, 3 pp.
Campanacci, M., Gui, L., Ranieri, L., Savini, R., "Treatment of Tibial Plateau Fractures", Chi. Org. Mov. 72(3), Dec. 1975 (Italian text), pp. 234-256, English Translation, 15 pp.
Kyphon Inc., Surgical Technique Manual Nov. 16, 1999, pp. 5, 6, 9, 16-19.
Kyphon web page, www.kyphon.com, Mar. 13, 2001, 1 p.
Signus Medical, TETRIS, Sep. 2003, 1 p.
Blackstone Medical Inc., Construx™ PEEK VBR System, 2005, www.blackstonemedical.com, 1 p.

\* cited by examiner

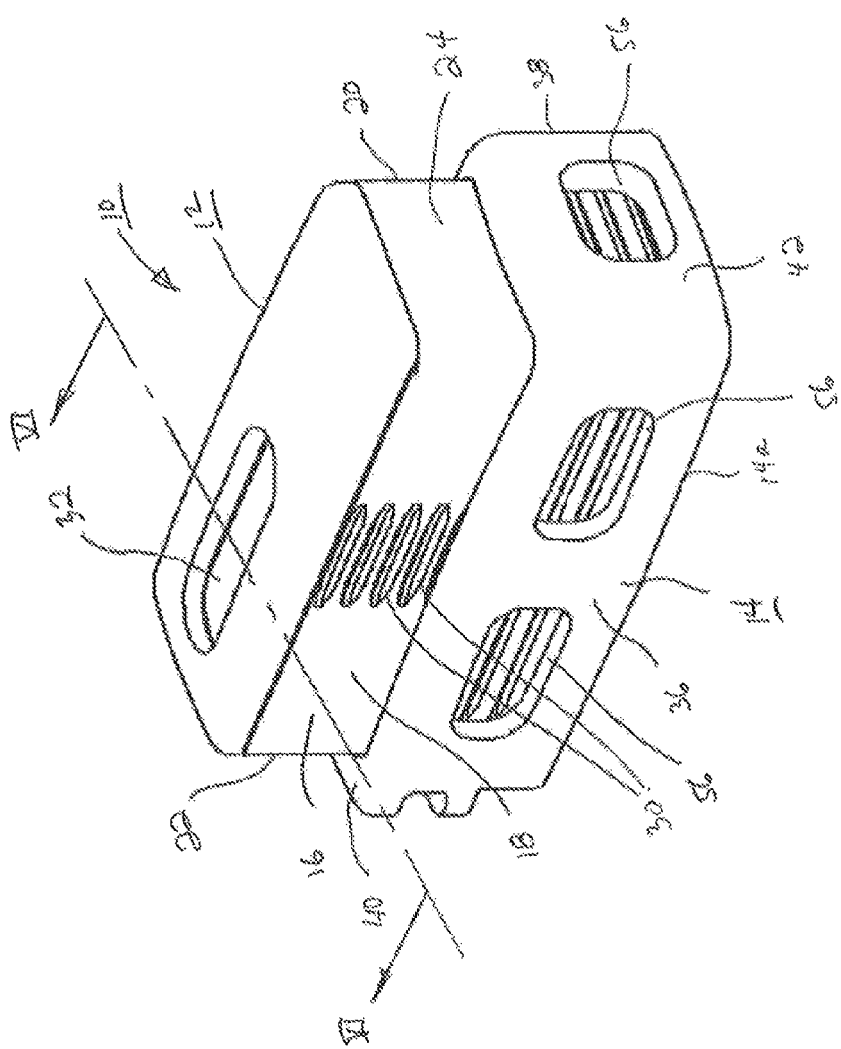

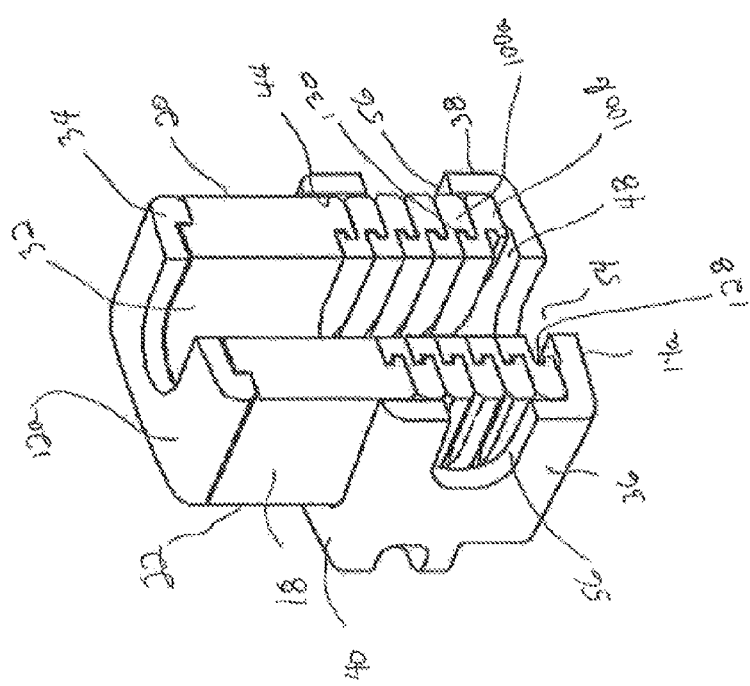

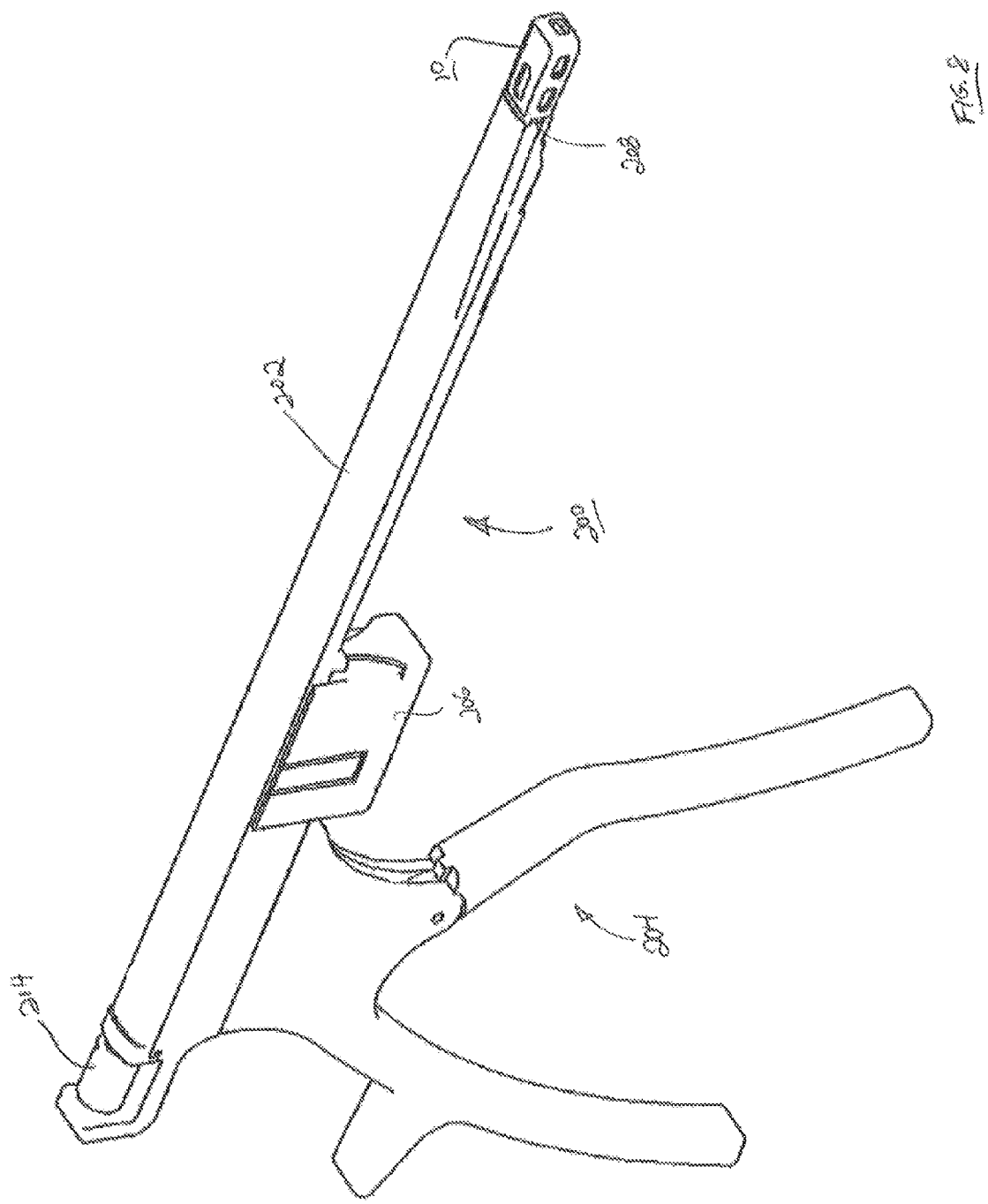

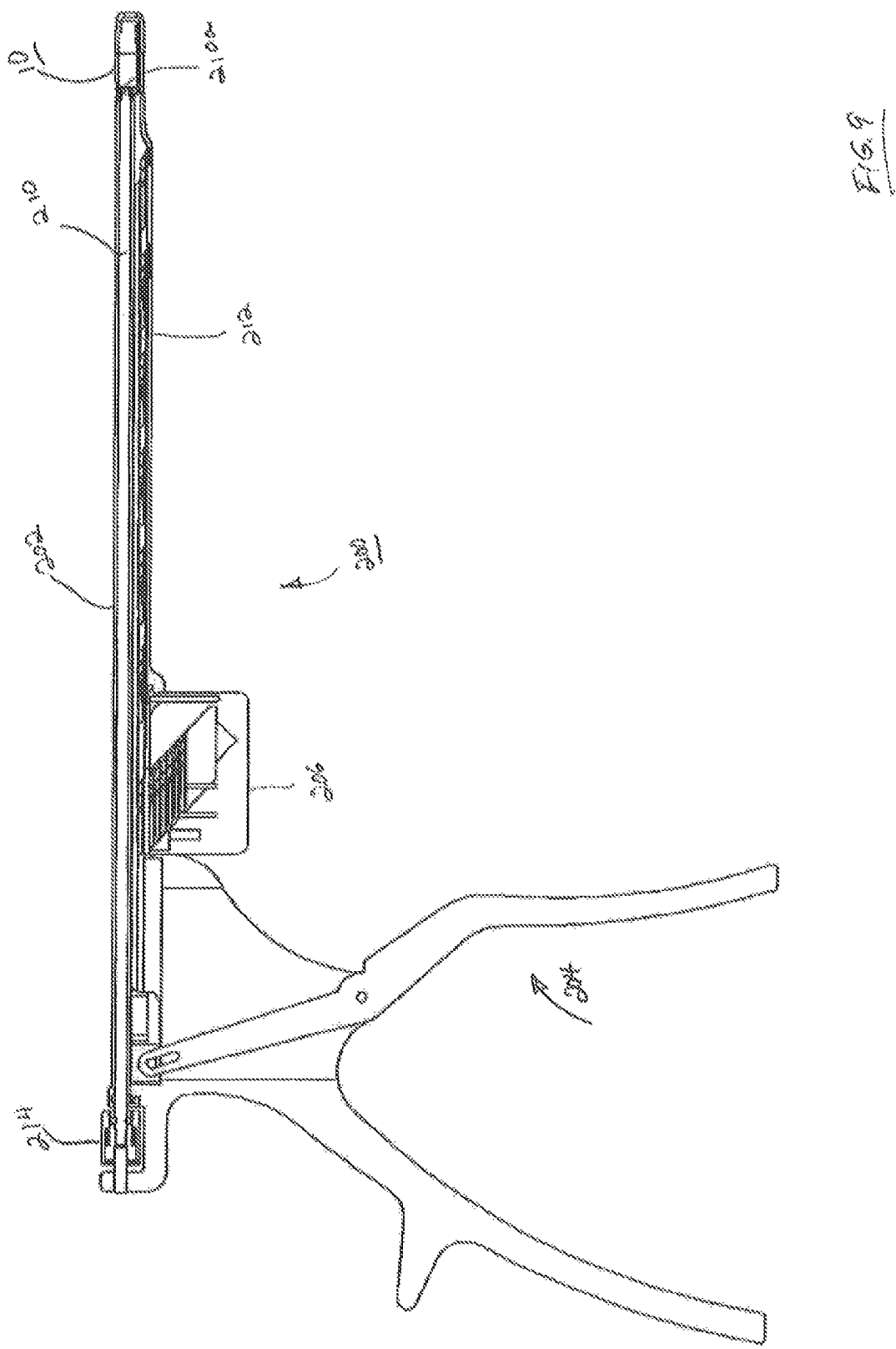

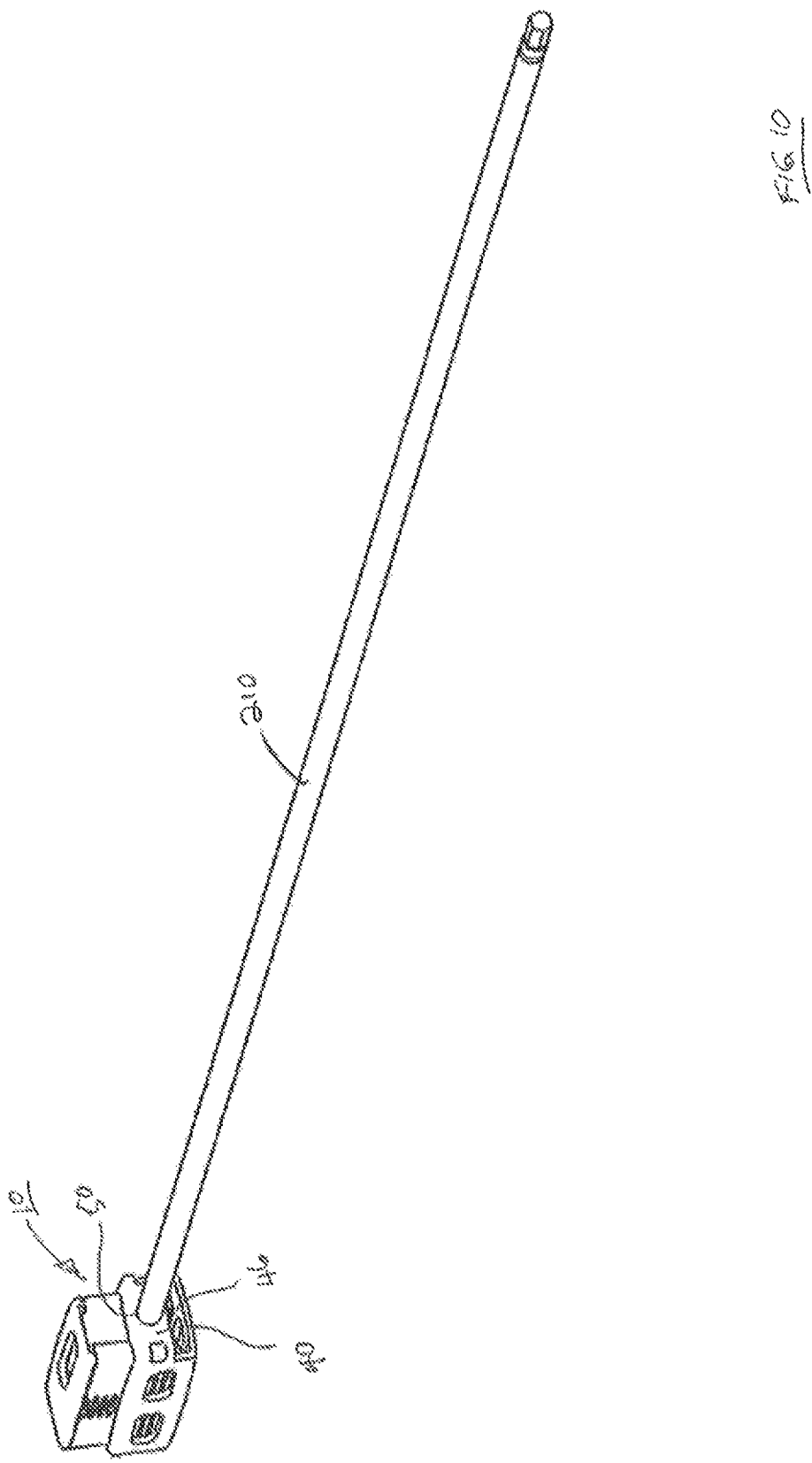

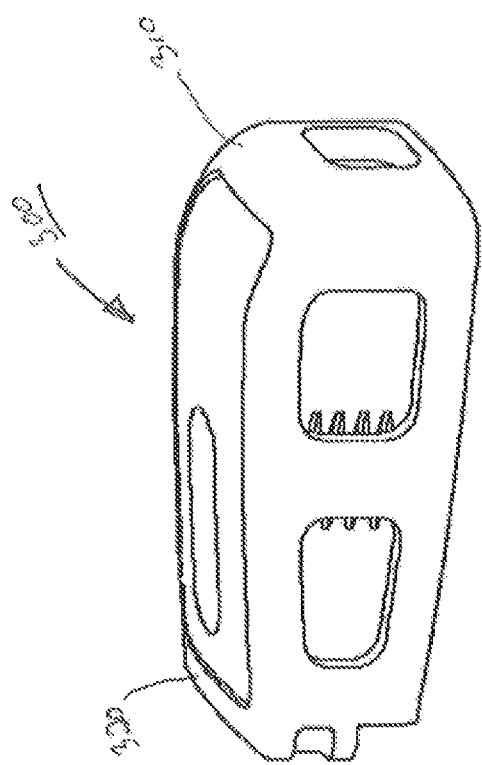

APPARATUS FOR USE IN SPINAL INTERBODY FUSION

CROSS-REFERENCE TO RELATED APPLICATION

This application is a continuation application of U.S. application Ser. No. 14/550,258, filed Nov. 21, 2014, now U.S. Pat. No. 9,517,141, which is a divisional application of U.S. application Ser. No. 13/795,054, filed Mar. 12, 2013, now U.S. Pat. No. 8,900,312, the entire contents of which are incorporated by reference herein.

FIELD OF THE INVENTION

The subject invention relates generally to the field of spinal implants and more particularly to expandable interbody fusion devices with graft chambers.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

Certain spinal devices for achieving fusion are also expandable so as to correct disc height between the adjacent vertebrae. Examples of expandable interbody fusion devices are described in U.S. Pat. No. 6,595,998 entitled "Tissue Distraction Device", which issued on Jul. 22, 2003 (the '998 patent), U.S. Pat. No. 7,931,688 entitled "Expandable Interbody Fusion Device", which issued on Apr. 26, 2011 (the '688 patent), and U.S. Pat. No. 7,967,867 entitled "Expandable Interbody Fusion Device", which issued on Jun. 28, 2011 (the '867 patent). The '998 patent, the '688 patent and the '867 patent each discloses sequentially introducing in situ a series of elongate inserts referred to as wafers in a percutaneous approach to incrementally distract opposing vertebral bodies to stabilize the spine and correct spinal height, the wafers including features that allow adjacent wafers to interlock in multiple degrees of freedom. The '998 patent, the '688 patent and the '867 patent are assigned to the same assignee as the present invention, the disclosures of these patents being incorporated herein by reference in their entirety.

Certain interbody fusion devices also include hollow portions or chambers that are filled with suitable material such as bone graft to promote fusion between vertebral bodies. The extent and size of the chambers establish areas of contact that are configured so as to assure maximum contact between the bone graft and the vertebral bodies. Sufficient surface area of the device surrounding the chambers needs to be maintained in order to provide an appropriate load bearing surface to withstand the compressive forces exerted by the opposing vertebral bodies. In addition, where expandable interbody fusion devices are used to correct height within the intradiscal space, the effect of shear forces on the expanded device due to torsional movement of the spine also needs to be considered.

Accordingly, there is a need to develop expandable interbody fusion devices with bone graft chambers that take into account and balance these factors, as well as to facilitate the introduction of bone graft into the device and through the graft chambers once expanded.

SUMMARY OF THE INVENTION

It is an object of the invention to provide an improved expandable device with openings serving as bone graft chambers for implantation into the intradiscal space between two opposing vertebral bodies of a spine having the facility for introducing bone graft thereinto upon expansion.

DESCRIPTION OF THE FIGURES

FIG. 6 is front perspective view of the expandable interbody fusion device FIG. 1 expanded to an expanded condition.

FIG. 7 is a perspective cross sectional view of the expanded device of FIG. 6 is seen along viewing lines VI-VI of FIG. 6.

FIG. 8 is a top perspective view of an inserter for inserting wafers releasably connected to the unexpanded device of FIG. 1.

FIG. 9 is longitudinal cross sectional view of the inserter of FIG. 8.

FIG. 10 is a perspective view of the guide used with the inserter of FIG. 8 releasably connected to the expanded device of FIG. 6.

FIG. 11 is a top perspective view of an alternative lordotic expandable fusion device.

DESCRIPTION OF THE EMBODIMENTS

Figure 1:
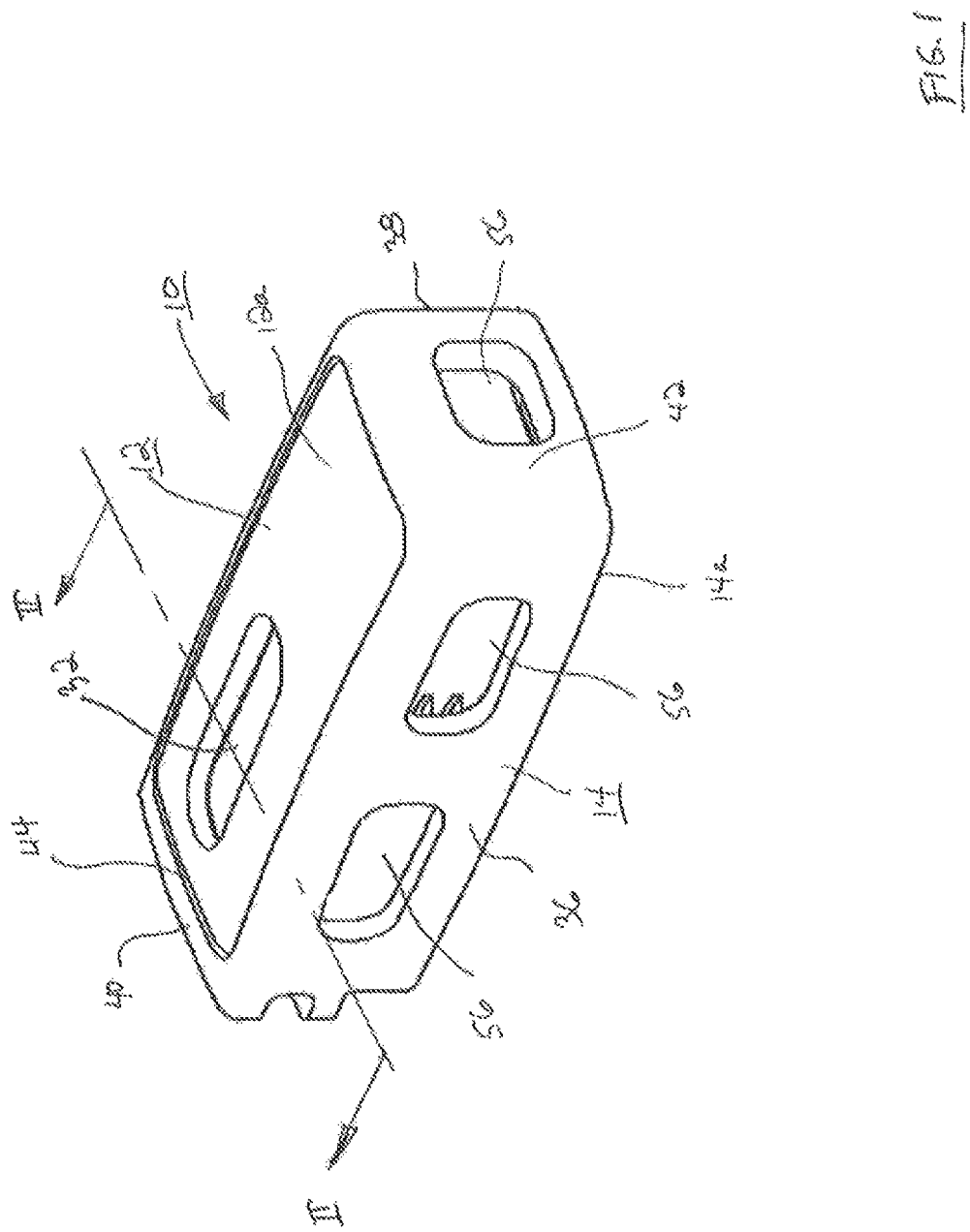
FIG. 1 is front perspective view of an expandable interbody fusion device in unexpanded condition in accordance with one embodiment of the present invention.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
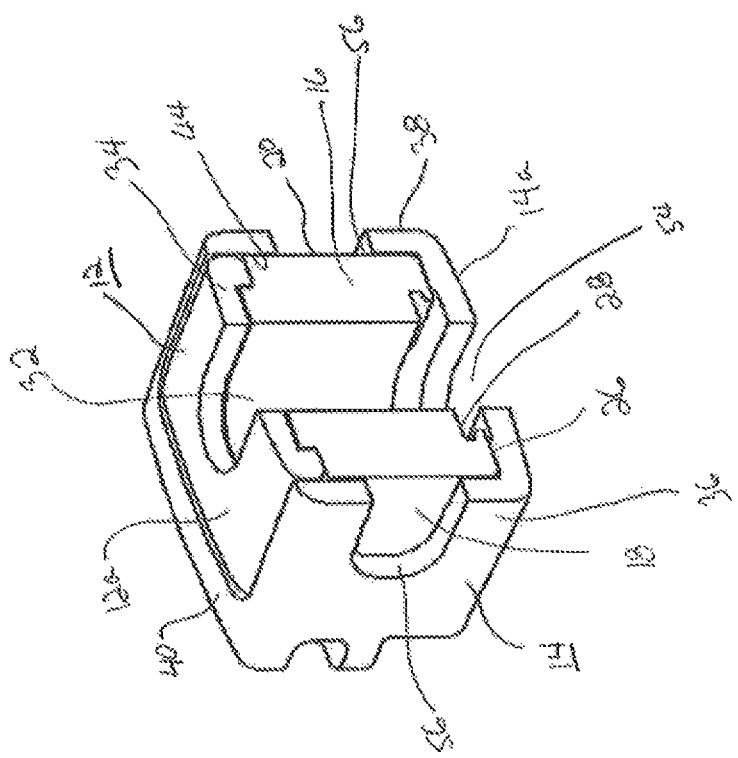
FIG. 2 is a perspective cross sectional view of the unexpanded device of FIG. 1 as seen along viewing lines II-II of FIG. 1.
Figure 3:
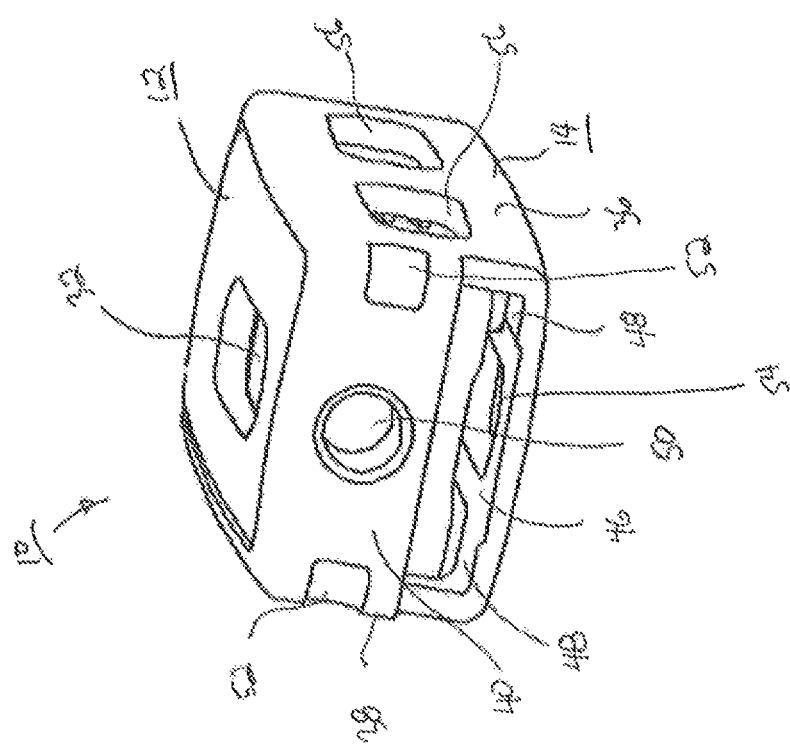
FIG. 3 is a rear perspective view of the device of FIG. 1.

In accordance with one embodiment of the invention, an expandable interbody fusion device 10 includes a first superior endplate 12 and a second inferior endplate 14, as shown in FIGS. 1-3. The interbody fusion device 10 has a height across the superior and inferior endplates 12, 14 in the unexpanded condition as illustrated in FIGS. 1-3 that is less than the normal anatomic height of a typical intradiscal space. The invention contemplates that a series of expansion members, such as interlocking wafers 100 as will be described, are introduced into the device 10 to distract the opposing vertebrae by separating the superior and inferior endplates 12, 14 in situ. Insertion of the wafers 100 separates the endplates 12, 14 to expand the height of the device within the intradiscal space and to ultimately restore the normal anatomic height of the disc space. Expansion devices of this type are shown and described in the '998 patent, the '688 patent and the '867 patent described hereinabove and incorporated herein by reference.

The present invention contemplates an improved interbody fusion device 10 that particularly includes openings that define graft chambers for containment of materials that promote bone fusion through the device between opposing vertebral bodies.

The superior endplate 12 as shown in FIGS. 1-3 and 6-7 is elongate and comprises a hub 16 having pair of side surfaces 18 and 20 extending longitudinally on each side of the hub 16 and a pair of end surfaces 22 and 24 extending respectively at the proximal rear end and the distal front end of the superior endplate 12. The hub 16 is sized and configured to fit within a cavity of the inferior endplate 14 for telescoping movement therewithin, as will be described. The lower surface 26 of the hub 16 (FIG. 2) includes a shaped configuration defined by wafer mating features 28 that are substantially identical to the mating features on the lower surface of each wafer 100, as will be described. The hub 16 defines a series of grooves 30 as shown in FIG. 6 extending along each side surface 18 and 20 thereof that is configured to engage ribs (not shown) projecting interiorly of the inferior endplate 14. This engagement temporarily holds the superior and inferior endplates together in the expansion direction as the device 10 is introduced into the intradiscal space to be distracted.

As shown particularly in FIGS. 1-3 and 6-7, the superior endplate 12 includes a graft chamber defined by an opening 32 extending through the upper outer surface 12a and the lower surface 26. In a particular arrangement, the opening 32 is situated to lie more adjacent to the proximal surface 20 or rear end of the device 10. In accordance with one arrangement, the superior endplate 12 is formed of a biocompatible polymer such as polyethylethylketone (PEEK). PEEK is used in fusion applications for its combination of strength, biocompatibility, and elasticity which is similar to human bone. Other composites may include derivatives of PEEK such as carbon fiber reinforced PEEK and PEKK, respectively. In a particular aspect, the superior endplate 12 may further include an upper endcap 34 that defines the outer surface 12a. Endcap 34 may be a separate plate formed of material for the promotion of bone growth, such as titanium, and may be attached to the endplate 12 with suitable conventional techniques. As an alternative, the upper surface 12a may be defined by a coating of a suitable layer of bone growth promotion material, such as titanium, which may be deposited by conventional techniques such as, for example, by ion implantation as described in U.S. Pat. No. 4,743,493, entitled "Ion Implantation of Plastics", issued on May 10, 1988 to Sioshansi et al., the contents of which are incorporated by reference herein.

The inferior endplate 14 of the interbody fusion device 10 as shown in FIGS. 1-3 and 6-7 is elongate and comprises a pair of opposing spaced apart sidewalls 36 and 38 extending along the longitudinal direction and projecting upwardly from the lower outer surface 14a. A pair of spaced apart endwalls 40 and 42 extend laterally across the device and project upwardly from outer surface 14a. Rear end wall 40 is disposed at the rear or proximal end of the device 10 and front end wall 42 is disposed at the front or distal end of the device 10. The side walls 36, 38 together with rear end wall 40 and front end wall 42 form an open, upwardly facing fully bounded interior cavity 44 as shown in FIGS. 1-2 and 7. The interior cavity 44 is sized and configured to receive the superior endplate 12 including the hub 16 and the endcap 34 in relatively close fit between the side walls 36 and 38 and the end walls 40 and 42 of the inferior endplate 14 in a non-expanded condition as shown in FIGS. 1 and 2. The hub 16 of superior endplate 12 remains fully contained within the inferior endplate 14 during telescoping expansion of the device 10 as shown in FIGS. 6 and 7, contributing to the torsional strength of the expanded device 10.

The inferior plate 14 as shown in FIG. 3 defines a fully bounded wafer channel 46 extending through the rear endwall 40 in communication with interior cavity 44 and through which the wafers 100 which serve as expansion members are introduced. The inferior endplate 14 includes a pair of opposite ledges 48 that define an upper support surface on which each wafer 100 is supported as it introduced into the wafer channel 46, as will be described. The ledges 48 define the bottom surface of the cavity 44. Wafers are introduced sequentially into wafer channel 46, as will be described. The rear endwall 40 further defines a threaded connection opening 50 for threaded releasable receipt of a guide pin for use in the introduction of wafers 100 and in the delivery of bone graft material into the device 10, as will also be described. Rear endwall 40 may also additionally include a pair of bilateral notches 52 adjacent the sidewalls 36 and 38 for use in attachment to portions of the wafer inserter for the establishment of a rigid connection to the device 10 for insertion into the intradiscal space.

As shown particularly in FIGS. 1-3 and 6-7, the inferior endplate 14 includes a graft chamber defined by an opening 54 extending through the lower outer surface 14a and the upper support surface 48 in communication with cavity 44. In a particular arrangement, the opening 54 is situated to lie more adjacent to the proximal surface 20 or rear end of the device 10 and at least in partial alignment with the opening 32 in superior endplate 12. In accordance with one arrangement, the inferior endplate 12 is formed of a material different from the material of the superior endplate 12. In this aspect, the inferior endplate 12 may be formed of a biocompatible metal, such as titanium, for its strength properties. Titanium is chosen for strength, biocompatibility, processing capability, and fluoroscopic imaging properties (radiolucency). Other alternative materials include cobalt chrome, stainless steel (both stronger than titanium but much less radiolucent), or biocompatible ceramics such as silicon nitride or zirconia, which are radiolucent. Titanium and silicon nitride have demonstrated good apposition to bone and superior to PEEK. In this regard where inferior endplate 14 is formed of titanium, the lower outer surface 14a would provide for the promotion of bone growth. Where inferior endplate 14 is not formed of a bone growth promotion material, lower outer surface 14a may be coated with a suitable layer of bone growth promotion material, such as titanium, and deposited in a conventional manner as described hereinabove.

Where inferior endplate 14 is formed of titanium or other suitable metal that is radiopaque, windows 56 may be formed through sidewalls 36 and 38 and/or through front endwall 42 as shown in FIGS. 1-3 and 6-7 so as to allow visual observation of the expansion of the device 10 upon insertion of the wafers 100 by suitable imaging techniques, such as fluoroscopy.

Figure 4:
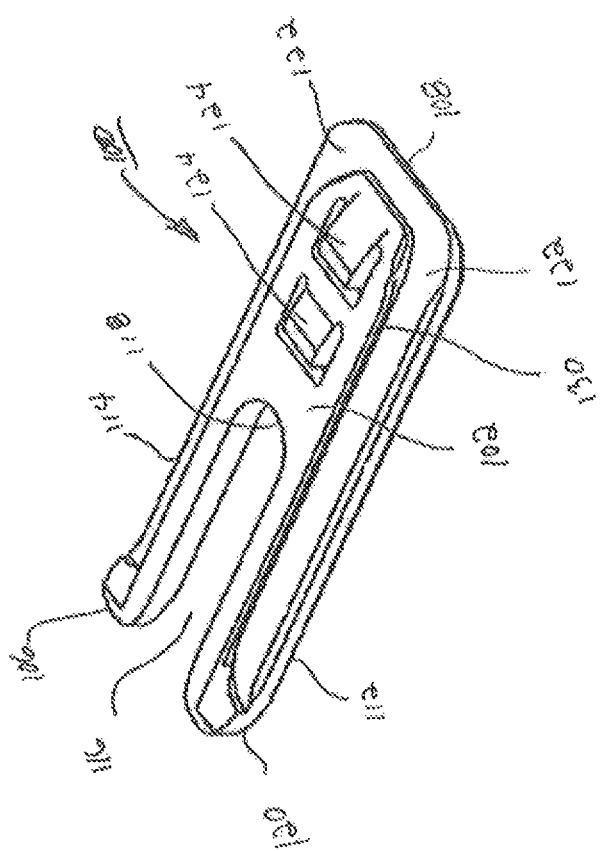
FIG. 4 is a top perspective view of an interlocking wafer serving as an expansion member to expand the interbody fusion device of FIG. 1.
Figure 5:
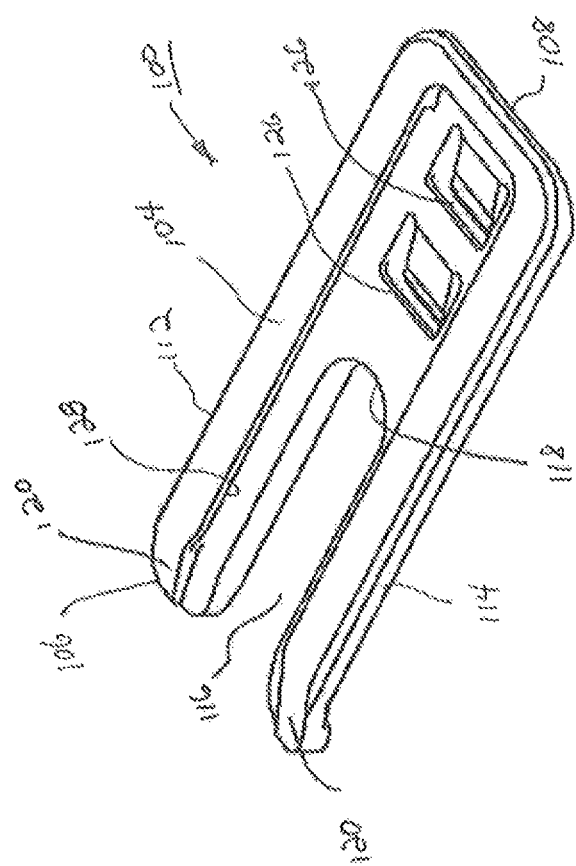
FIG. 5 is a bottom perspective view of the interlocking wafer shown in FIG. 4.

Details of an interlocking wafer 100 are shown in FIGS. 4-5. The wafer 100 is elongate and has an upper surface 102 and a lower surface 104, both of which are generally planar so that the wafers can form a stable stack within the interbody fusion device 10. Wafer 100 includes a trailing rear end 106 and a leading front end 108. The rear end 106 is formed substantially in the form of a horseshoe, with a pair of spaced opposing arms 112 and 114 defining an open rearward facing generally U-shaped opening 116. The surface 118 between the upper surface 102 and the lower surface 104 at the base of opening 116 defines a pushing surface, as will be described. The opening 116 at the rear end of each wafer 100 is provided to allow bone graft material to flow into the device 10 through the openings 116 and into the openings 32 and 54 extending through the superior endplate 12 and the inferior endplate 14, respectively.

The rear end 106 includes a downward-facing sloped surface 120 at the free end of each arm 112 and 114 that corresponds angularly to an upward-facing surface 122 on the leading front end 108 of the wafer 100. The sloped surfaces help displace an earlier inserted wafer 100 upon introduction of a new wafer. More specifically, when a first wafer 100a is introduced through the wafer channel 46, resting on the ledges 48, the downward-facing sloped surface 120 thereof is lifted upon contact with the upward-facing slope 122 of a newly inserted wafer 100b (FIG. 7). This allows the newly inserted wafer to ride along the ledges 48 until it is positioned fully underneath the previous wafer as more fully described in the '867 patent.

The wafer 100 includes several features for interlocking engagement to the hub 16 and to adjacent wafers 100 in a complementary interlocking mating interface. One particular feature includes a series of locking elements defined by resiliently deflectable prongs 124 that project outwardly above the upper surface 102 of the wafer 100 in the direction of expansion of device 10. A complementary series of locking surfaces 126 are defined in the lower surface 104 of the wafer 100 for resilient engagement with the prongs 124 as wafers are inserted into device 10 to form a stack. It should be appreciated that the prongs 124 and associated locking surfaces 126 may be formed on either the upper surface or the lower surface of a wafer 100 as desired. The lower surface 104 of each wafer 100 as shown in FIGS. 5 and 7 also defines a T-slot configuration 128 for mating with a T-bar configuration 130 on the upper surface 102 of a successive wafer 100 as shown in FIGS. 4 and 7. It should be appreciated that the respective T-bar and T-slot configurations may also be formed on either the upper surface or the lower surface of a wafer 100 as desired. In the illustrated arrangement, there are two prongs 124 extending generally linearly and substantially centrally along the elongate longitudinal direction adjacent the front end 108 of wafer 100. The structure and function of a wafer 100 and the prongs 124 are more fully described in the '867 patent, incorporated herein by reference.

The superior and inferior endplates 12 and 14 are configured to be initially releasably engaged by the ribs (not shown) and the grooves 30 when the device 10 is unexpanded, as shown in FIGS. 1 and 2. In this unexpanded condition, the device 10 is attached to an inserter 200 as shown in FIGS. 8 and 9. In this stage, the hub 16 is disposed within the cavity 44 of inferior endplate 14 with the ribs (not shown) on the interior surfaces of side walls 36, 38 engaging the grooves 30 extending along each side of the hub 16. The lower surface 26 of hub 16 is on or closely adjacent to the wafer support ledges 48 in facing relationship. This engagement temporarily holds the superior and inferior endplates together as the device 10 is introduced into the intradiscal space to be distracted. In this unexpanded condition the outer surface 12a of the superior endplate 12 is substantially flush with the upper surfaces of the sidewalls 36 and 38 as illustrated in FIGS. 1 and 2. In addition to providing strength for the device 10 as described hereinabove, such nesting of the superior endplate 12 within inferior endplate 14 allows for lower height of the unexpanded device 10.

The inserter 200 as illustrated in FIGS. 8 and 9 comprises a track assembly 202 and a handle 204 for individually sequentially inserting a plurality of wafers 100 supported linearly within the track assembly 202. A source of wafers 100 is provided in a cartridge 206 supported by the track assembly 202. A pair of opposing fingers 208 is provided at the distal end of the track assembly 202, fingers 208 releasably engaging the notches 52 in the rear endwall 40 for connection thereto. As depicted particularly in FIG. 9, the track assembly 202 supports an elongate guide pin 210 the distal end 210a of which is threaded for releasable threaded connection with threaded opening 50 in rear endwall 40 of the device 10. Inserter 200 comprises an elongate driver 212 that is translatably supported within the track assembly 202, the distal end of which is configured to enter the rearward facing opening 116 of each wafer 100 and engage the pushing surface 118. Upon actuation of the handle and translation of the driver 212, the wafer 100 is suitably moved through the channel 46 and into the device 10 by the force of the distal end of the driver 212 against the pushing surface 118. Inserter 200 further includes a quick disconnect member 214 which upon rotation allows the inserter 200 to be detached from the guide pin 210, thereby leaving the guide pin 210 releasably connected to the expanded device 10 after suitable insertion of the desired number of wafers, as shown in FIG. 10. With the guide pin 210 attached to the device 10 at opening 50, the channel 46 extending through the rear end wall 40 of device 10 is fully exposed and may be used for the introduction of suitable bone graft material into expanded device 10. For the introduction of a bone graft material, the guide pin 210 may be used as a locator for subsequent attachment to an apparatus containing such bone graft material whereby such apparatus may be supported by the guide pin 210 while allowing access into channel 46. Further details of the structure and operation of the inserter 200 are described in commonly assigned U.S. Pat. No. 6,997,929, entitled "Tissue Distraction Device", and issued Feb. 14, 2006, the contents of which are incorporated by reference herein.

The manner in which the interbody fusion device 10 is expanded is illustrated in FIGS. 6-7. When the first wafer 100 is introduced, the interlocking features on the upper surface 102 of the wafer 100 engage the mating features 28 on the lower surface 26 of superior endplate 12 lifting the superior endplate 12 upwardly within the cavity 44 between sidewalls 36, 38 and breaking the initial releasable engagement. When the first inserted wafer 100 is introduced into the device 10 the rearward facing opening 116 in the wafer 100 is located to be in at least partial alignment and communication with the openings 32 and 54 extending through the superior endplate 12 and inferior endplate 14, respectively. This process continues with each successive wafer 100 inserted beneath a previously inserted wafer 100 until a complete stack is formed telescopically lifting the superior endplate 12 relative to the inferior endplate 14, as depicted in FIG. 7. As each subsequent wafer 100 is introduced, the prongs 124 lockingly engage the mating locking surfaces 126 features on the lower surfaces of each previously introduced wafer 100, with the openings 116 of each wafer 100 being disposed such that they are in at least partial alignment and communication with the openings 116 of each previously introduced wafer 100. The lowermost wafer 100 is supported on the support surfaces of ledges 48 with the rearward facing opening being in direct communication with the channel 46 extending through rear endwall 40 of inferior endplate 14. It should be noted that all the wafers 100 are contained within and constricted by the opposing side walls 36, 38 and the rear and front end walls 40, 42 so as to provide additional resistance against torsional movement of the spine. The inserter 200 is released from the expanded interbody fusion device 10 upon unthreading the guide pin 210 from opening 50.

Having described the interbody fusion device 10, a suitable bone filler or bone graft to promote fusion between opposing vertebral bodies may be inserted into the expanded device 10 as well as into the intradiscal space adjacent to device 10. With the inserter 200 used to insert inserts such as wafers 100 into device 10 having been removed from the expanded device 10, it can be appreciated that the wafer insertion channel 46 provides clear and unobstructed access into the expanded device 10 and into the rearward facing openings 116 of wafers 100, facilitating the introduction of bone graft material. A suitable graft insertion instrument using the guide pin 210 as a locator may be used to inject bone graft under pressure into the expanded device 10. Under an appropriate pressure, such bone graft will flow through into channel and openings 116 and into the openings 32 and 56 of superior endplate 12 and inferior endplate 14. Injection of the bone graft will continue until the graft is stress loaded against the endplates of the opposing vertebral bodies. In some instances, bone graft may be pre-loaded into an unexpanded device 10 prior to insertion of the device 10 into the intradiscal disc space. Suitable bone graft materials may include autograph bone, allograft bone, bone morphogenic protein (BMP) and xenograft and synthetic derived bone substitutes, as described for example, in the '998 patent. It should also be understood that a material with a bone fusion promoting substance, such as a sponge saturated with BMP, may be placed in the openings 32 and 54 suitably formed to support such a sponge. This will allow the fusion promoting substance to be pre-loaded into device 10 and not be disrupted upon expansion of device 10 by insertion of wafers 100 as described herein.

It is contemplated that the wafers 100 described herein, be formed of a biocompatible material that is sufficiently rigid to form a solid stack as the successive wafers are inserted into the device. Thus, in one specific embodiment, the wafers 100 are formed of PEEK or a carbon-fiber reinforced PEEK, or similar polymeric material.

In accordance with certain specific applications, the overall length of the device 10 as shown in FIGS. 1 and 6, as defined by the length of the inferior endplate 14, is about 25 mm. The width of the device is approximately 9 mm. The height of the unexpanded device 10 of FIGS. 1-2 with the superior endplate 12 fully nested within the inferior endplate 14 is approximately 7 mm. With the introduction of five wafers 100, each of which has a thickness of approximately 1.0 mm, the height of device 10 may be expanded from an unexpanded height of approximately 7 mm to an expanded height of approximately 12 mm. Of course, the number of wafers may vary depending upon the particular surgery and the initial height may also be different. For example, device 10 may be formed to have an initial unexpanded height of approximately 9 mm and with the addition of seven wafers 100, each having a thickness of 1 mm, the height of device 10 may be increased to approximately 16 mm. As such, it should be appreciated that these dimensions are only illustrative and that the dimensions of the device 10 and the number of wafers 100 to be inserted and their thicknesses may vary depending upon the application.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, as shown in FIG. 11, a device 300 embodying the features described herein may be formed to have a lordotic shape, whereby the leading front end 310 intended to be placed in the anterior portion of the intradiscal space may have a height greater than the trailing rear end 320, intended to be placed in the posterior portion of the intradiscal space.

What is claimed is:

1. An apparatus for use in spinal interbody fusion, comprising:
    an expandable device including a first outer surface for contacting one vertebral body in a spine and a second outer surface for contacting a second opposing vertebral body in said spine, a front end and a rear end, and a channel extending into said expandable device;
    an inserter releasably attached to said expandable device at said rear end, said inserter including a track assembly having a distal end and a proximal end; and
    a guide pin releasably connected to said expandable device and detachably connected to said inserter, said guide pin being supported by said track assembly and being detachable therefrom, said guide pin remaining releasably connected to said expandable device upon detachment of said inserter from said expandable device and said guide pin, said guide pin being configured to serve as a locator for subsequent attachment to another apparatus, including an apparatus for introducing bone graft material into said expandable device through said channel.

2. The apparatus of claim 1, wherein said expandable device comprises a first opening through said first outer surface and a second opening through said second outer surface, said channel communicating with said first opening and said second opening, said guide pin being releasably connected to said expandable device at a location spaced from said channel.

3. The apparatus of claim 2, wherein said expandable device comprises a first endplate defining said first outer surface and said first opening therethrough, and a second endplate defining said second outer surface and said second opening therethrough, said first endplate and said second endplate being movable relative to each other in an expansion direction.

4. The apparatus of claim 2, wherein said channel extends through said rear end of said expandable device.

5. The apparatus of claim 2, wherein said rear end of said expandable device includes an attachment surface for releasable attachment of said inserter.

6. The apparatus of claim 5, wherein said attachment surface includes at least one notch adjacent the rear end of said second endplate.

7. The apparatus of claim 6, wherein said inserter includes a distal end comprising at least one finger releasably engaged in said at least one notch.

8. The apparatus of claim 5, wherein said guide pin is elongate having a distal end and a proximal end, the distal end having a threaded extent, and wherein said attachment surface includes a threaded opening in receipt of said threaded extent of said guide pin.

9. The apparatus of claim 1, wherein said inserter includes a rotatable quick disconnect member at the proximal end of said track assembly for allowing said track assembly to be detached from said guide pin while said guide pin remains releasably connected to said rear end of said second endplate.

10. The apparatus of claim 1, wherein said inserter supports a plurality of inserts for sequential insertion into said channel, one beneath the other, each of said inserts having a rearward facing opening and a pushing surface engaged by a driver of said inserter to insert said inserts into said expandable device.

11. The apparatus of claim 1, wherein said track assembly supports at least one insert for insertion into said expandable device through said channel through the rear end of said expandable device for causing expansion of said expandable device.

12. The apparatus of claim 11, wherein said track assembly further comprises an elongate driver translatably movable thereon, said driver having a distal end and a proximal end, the distal end being configured to engage said insert and drive said insert into said expandable device through said channel.

13. The apparatus of claim 12, wherein said insert comprises an elongate body having a front end, a rear end, and a rearward facing opening defining a U-shaped opening, a base of said opening defining a pushing surface.

14. The apparatus of claim 13, wherein said driver is sized and configured to enter said U-shaped opening of said insert and engage said pushing surface of said insert.

15. The apparatus of claim 11, wherein said inserter includes an actuator attached to said track assembly and operable to translatably move said insert into said expandable device while said guide pin is connected to said expandable device.

\* \* \* \* \*